(12) United States Patent
Wagenheim

(10) Patent No.: US 6,591,872 B2
(45) Date of Patent: Jul. 15, 2003

(54) PROCESS AND PLANT FOR THE DYNAMIC PACKAGING OF GASES, ESPECIALLY THOSE FOR MEDICAL USE

(75) Inventor: Serge Wagenheim, Sartrouville (FR)

(73) Assignee: Air Liquide Sante (International), Paris (FR)

( * ) Notice: Subject to any disclaimer, the term of this patent is extended or adjusted under 35 U.S.C. 154(b) by 0 days.

(21) Appl. No.: 09/906,609

(22) Filed: Jul. 18, 2001

(65) Prior Publication Data

US 2002/0020462 A1 Feb. 21, 2002

(30) Foreign Application Priority Data

Jul. 18, 2000 (FR) .............................. 00 09412

(51) Int. Cl.⁷ ................................................ B65B 3/04
(52) U.S. Cl. ................................ 141/2; 141/9; 141/82; 141/104; 141/105; 137/5; 48/189.1
(58) Field of Search ........................... 141/2, 9, 18, 22, 141/37, 39, 47, 63, 82, 83, 100, 104, 105; 137/3, 5, 88, 93; 128/204.17, 203.12; 48/180.1, 189.1

(56) References Cited

U.S. PATENT DOCUMENTS

| | | | |
|---|---|---|---|
| 3,593,735 A | * | 7/1971 | Reiher ......................... 137/88 |
| 4,345,612 A | | 8/1982 | Koni et al. |
| 4,860,803 A | * | 8/1989 | Wells ............................. 141/9 |
| 5,636,626 A | | 6/1997 | Bloch et al. |
| 5,690,968 A | * | 11/1997 | Ross et al. ................... 424/718 |

FOREIGN PATENT DOCUMENTS

| | | |
|---|---|---|
| EP | 0 566 488 | 10/1993 |
| FR | 2 532 858 | 3/1984 |
| FR | 2 548 549 | 1/1985 |
| GB | 1 382 338 | 1/1975 |

* cited by examiner

Primary Examiner—Timothy L. Maust
(74) Attorney, Agent, or Firm—Young & Thompson

(57) ABSTRACT

A process for the dynamic manufacture and packaging of gas mixtures containing a first component and a second component in predefined proportions, the first and second components being chosen from the group formed by $O_2$, $N_2$, He and $N_2O$, in which predetermined proportions of the first and second components are dynamically mixed in order to obtain a gas mixture of the desired composition and the temperature of the mixture is adjusted in order to keep it above the demixing threshold temperature of the mixture. This process is particularly suitable for the production of analgesic gas mixtures that can be used in the medical field, particularly a mixture formed from 50% oxygen and 50% nitrous oxide.

15 Claims, 1 Drawing Sheet

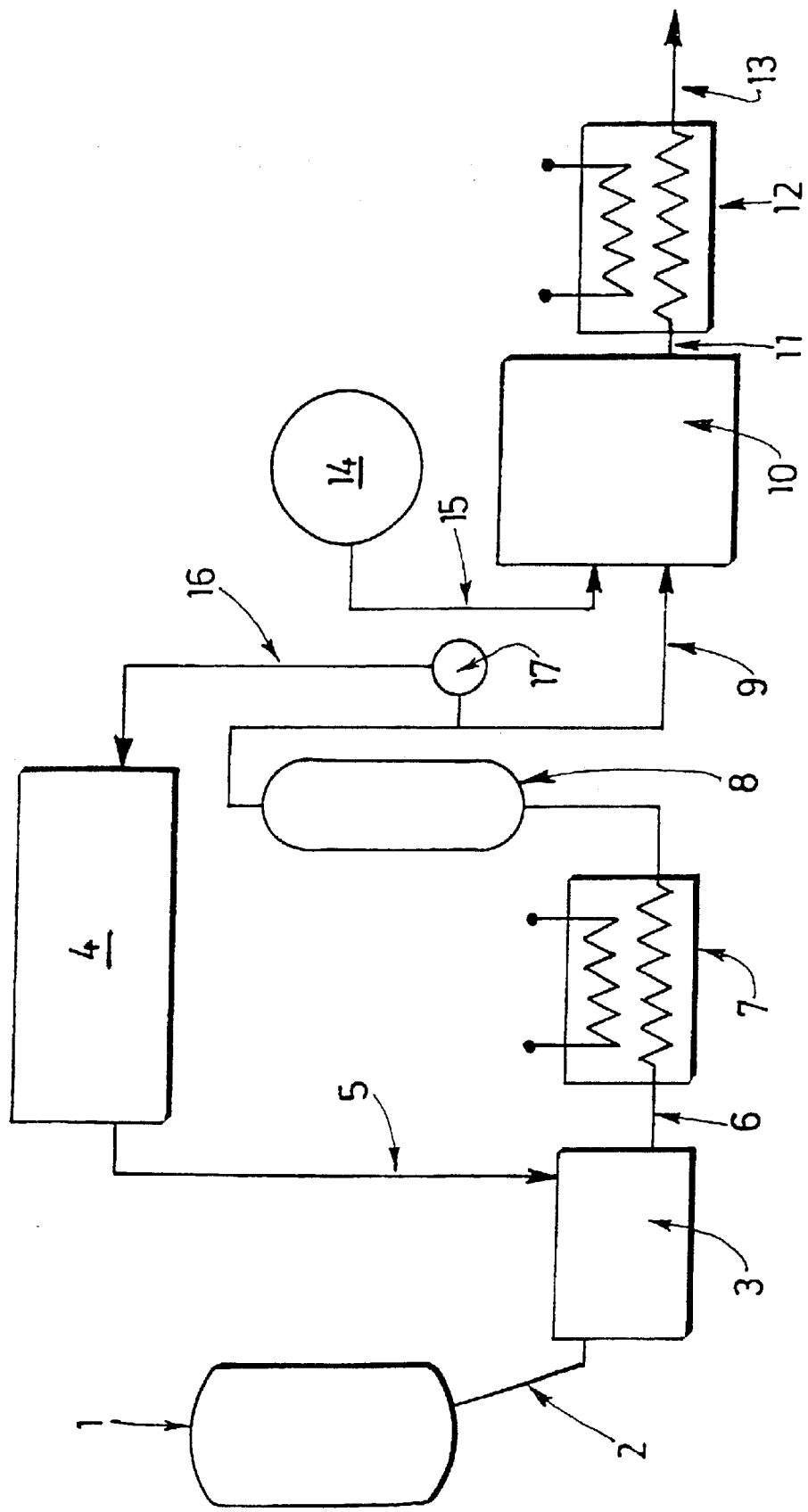

PROCESS AND PLANT FOR THE DYNAMIC PACKAGING OF GASES, ESPECIALLY THOSE FOR MEDICAL USE

FIELD OF THE INVENTION

The invention relates to a plant for dynamically manufacturing and for packaging medical gas mixtures, particularly $N_2O/O_2$ gas mixtures that can be used in the medical field, especially in analgesia, preferably $N_2O/O_2$ mixtures containing approximately 50 vol % nitrous oxide ($N_2O$) and 50 vol % oxygen.

BACKGROUND OF THE INVENTION

From the industrial standpoint, there are at the present time various methods and processes for manufacturing and packaging gas mixtures.

However, in these the amounts of gas to be mixed are fed into a gas mixer and are monitored by measuring the pressure and the temperature of the gases. The metering is therefore based on two measuring instruments which add their measurement errors, thus possibly leading to quite random results.

Moreover, the choice of measurement points in the plant does not allow the desired physical quantities to be determined, or does so only incompletely, and therefore does not allow the mixture to be produced effectively or reliably.

Thus, the temperature is usually measured at the gas-filling injection rail by a temperature probe which does not reflect, or does so only very inaccurately, the effective gas temperature in the packaging containers.

Sometimes this measurement is performed directly on the surface of the container (bottle) by an infrared thermal probe; it will be understood that this measurement is not a precise reflection of that of the gas in the container.

Moreover, a pressure sensor is used to constantly measure the pressure in the filling injection rails, the gases while flow through the pipes.

Consequently, there is therefore an inevitable difference between the final pressure in the containers, at the end of filling, and the pressure measured during filling, which depends on the pressure drops, the flow rate and the temperature of the gases.

Not knowing the pressure-drop coefficients and the temperature of the gases precisely therefore requires the pressure to be checked in static mode, at the end of the injection cycle, that is to say a posteriori.

Thus, if the amounts of gas mixed are off-specification, it is then necessary to top up the amounts of gas mixed by adding the amount of gas lacking, something which is not practical or not always easily achievable.

However, conversely, any excess gas completely falsifies the precision of the desired gas mixture and either results in the gas mixture thus obtained being scrapped or requires a readjustment in order to try to re-establish the equilibrium. This is not always possible.

Furthermore, a process for packaging gas mixtures based on carbon dioxide ($CO_2$) is also known, this process being called a dynamic packaging process, in which the $CO_2$ is packaged above a supercritical state at a pressure of 270 bar and at a temperature between about 70° C. and 120° C., both the pressure and the temperature of the gas being determined by the conditions under which the packaging process is carried out.

The pressures of the various gas sources must be balanced at 270 bar since the pressure is defined in such a way that containers can be filled at a pressure of 200 bar even in summer when they are hot, since they are usually stored outdoors. This means that the filling source downstream of the mixing chamber must therefore be able to reach 240 bar (for a container at a temperature ranging up to 60° C.).

In addition, the pressure drops across such a dynamic mixer often reaches 20 bar and consequently the pressures of the gas sources must reach a minimum of 260 bar.

Hitherto, $CO_2$ is the only liquefied gas that has already been packaged dynamically.

During a filling cycle, the pressures of the gas sources are reduced downstream of the mixing chamber down to the pressure of the containers and the pressure downstream of the chamber varies, during the cycle, from a few mbar to the final filling pressure of the gas mixture.

In the case of $CO_2$ at a pressure of 270 bar, the temperature is 70° C. and this is chosen so that the expansion is not accompanied by a change of state of the $CO_2$, passing into the solid state (carbon dioxide snow) especially when the pressure is less than 5 bar.

This is because any formation of carbon dioxide snow runs the risk of obstructing the taps of the bottles, thus resulting in disparities in the contents of the gas mixtures produced in the bottles for the same filling injection rail.

Consequently, only gas mixtures containing a $CO_2$ content generally not exceeding 30% can be produced, since otherwise the temperature reached downstream of the expansion chamber would be below the demixing temperature.

Gas mixtures whose content of a given component is greater than 30% (by volume) are usually produced by more conventional manufacturing methods, for example by gravimetry with a check of the masses injected into the bottles by weighing or by a temperature-corrected pressure measurement. However, these methods have the drawbacks of making it almost mandatory to roll the bottles after mixing in order to homogenize the contents thereof and to carry out an analytical check on the containers in order to ensure that they conform to the intended specifications. Such procedures are therefore not very practical and are expensive in terms of time and of productivity.

Furthermore, during dynamic mixing there is also the problem of demixing of the gas mixture downstream of the mixing chamber, that is to say inopportune demixing or separation of the various components of the mixture downstream of the site where the said mixing takes place.

Demixing of a gas mixture is characterized by the separation of the said mixture into two separate phases, namely a gas phase and a liquid phase.

Demixing occurs as soon as the temperature of the mixture drops below a temperature threshold. The higher the gas content of the mixture the higher the demixing temperature.

For a binary gas mixture formed from 50% $O_2$ and 50% $N_2O$, this demixing threshold is about −5.5° C., as explained in the document *"Equilibria for mixtures of oxygen with nitrous oxide and carbon dioxide and their relevance to the storage of $N_2O/O_2$ cylinders for use in analgesia"*, March 1970.

Now, gas packaging using a dynamic mixer is always accompanied by an expansion downstream of the mixing chamber and therefore in general a reduction in the temperature of the gases, even to below the demixing temperature in the case of an analgesic mixture.

The flow of the gases through the filling injection rails into the bottles is therefore a two-phase flow, the liquid phase and the gas phase moving at different flow velocities.

Consequently, the bottles are no longer filled homogeneously and relatively large differences are observed in the final contents of the mixtures produced in each of the bottles filled from the same injection rail during the same manufacturing cycle or process.

These disparities may be explained by preferential flows of certain constituents of the gas mixture with respect to others in the pipes of the injection rails for filling the containers, namely gravitational flows or flows in the form of droplets in the case of liquefied gases.

Thus, under high filling-rate conditions or in the case of type B5 small-volume (5 liter) containers, the resulting contents of mixtures in a few containers of the same manufacturing batch may be outside the production tolerances imposed by the Pharmacopoeia, namely a maximum deviation of 1% in the case of a 50 vol %/50 vol % $O_2/N_2O$ mixture. Consequently, it is essential to carry out an analytical check on each container. This is tiresome and not very practical from the industrial standpoint.

SUMMARY OF THE INVENTION

Thus, it is an object of the present invention to be able to produce gas mixtures, in particular gas mixtures intended for the medical field, and then to package them rapidly, reliably and effectively, that is to say without encountering the problems that arise with the conventional packaging processes.

Put another way, the problem that arises is to be able to produce and package, dynamically, gases for producing gas mixtures containing mainly one or several of the following constituents $O_2$, $CO_2$, $N_2$, He and $N_2O$ in predefined proportions so as to allow the production of mixtures having a variable content of a given gas, especially $CO_2$ and $N_2O$ in contents greater than 30%, in particular a process that can be used for producing medical gas mixtures, for example 50 vol %/50 vol % oxygen/nitrous oxide analgesic binary gas mixtures, while preventing the gas mixture thus produced from reaching its demixing temperature threshold or point.

In other words, the process of the invention should have the advantages of the known $CO_2$ dynamic packaging process without having its drawbacks, that is to say to be able to be used to manufacture gas mixtures having, in particular, a content of more than 30% of a given gas, such as nitrous oxide ($N_2O$) or oxygen, while minimizing or preventing as far as possible the demixing phenomenon.

It follows that the solution provided by the present invention relies on a process for manufacturing gas mixtures containing at least a first component and at least a second component in predefined proportions, the said first and second components being chosen from the group formed by $O_2$, $N_2$, He and $N_2O$, in which:

(a) predetermined proportions of at least the said first component and the said second component are mixed dynamically in order to obtain a gas mixture of the desired composition;

(b) the temperature of the said gas mixture containing the said first and second components obtained in step (a) is adjusted in order to keep it above the demixing threshold temperature of the said mixture.

According to another aspect, the invention also relates to a process for manufacturing gas mixtures containing at least a first component and at least a second component in predefined proportions, the said first component being chosen from the group formed by $O_2$, $N_2$, He and $N_2O$ and the said second component being $CO_2$, in which:

(a) predetermined proportions of at least the said first component and the said second component are mixed dynamically in order to obtain a gas mixture of the desired composition;

(b) the temperature of the said gas mixture containing the said first and second components obtained in step (a) is adjusted in order to keep it above the demixing threshold temperature of the said mixture.

Depending on the case, the manufacturing process of the invention may include one or more of the following characteristics:

the second component is chosen from $CO_2$ and $N_2O$ and the content of the second component ($N_2O$ or $CO_2$) is greater than or equal to 30 vol %, preferably at least 40 vol %;

the first component is oxygen and the second component is nitrous oxide ($N_2O$) and preferably the gas mixture consists of 50 vol % of the said first component and 50 vol % of the said second component, the first component being oxygen and the second component being nitrous oxide ($N_2O$);

at least one of the said first and second components is in the supercritical state;

in step (b), the temperature of the gas mixture is adjusted to or kept above $-5.5°$ C.;

the temperature of the gas mixture is adjusted by warming the gas mixture by heat exchange, preferably the said warming being carried out by at least one electric heater;

the gas mixture contains $CO_2$ and $O_2$, and possibly helium;

the pressure of the gas mixture is between 120 bar and 300 bar;

at least a first component and at least a second component in predefined proportions in at least one container, particularly a gas bottle, the said gas mixture being obtained by a gas mixture manufacturing process;

a gas mixture consisting of 50 vol % oxygen and 50 vol % nitrous oxide ($N_2O$) in at least one container, in particular a gas bottle, the said gas mixture being obtained by a gas mixture manufacturing process.

The invention also relates to a plant for manufacturing, dynamically, gas mixtures containing at least a first component and at least a second component in predefined proportions, comprising:

a source of the first component, containing the said first component;

a source of the second component, containing the said second component;

at least one dynamic mixing chamber for mixing the said first and second components in order to obtain a gas mixture of the desired composition; and temperature adjustment means located downstream of the said mixing chamber allowing the temperature of the said gas mixture containing the said first and second components to be adjusted or kept above the demixing threshold temperature of the said gas mixture.

Preferably, the plant may include one or more of the following characteristics:

the temperature adjustment means are chosen from heat exchangers and preferably electric heaters;

compression means located upstream of the said chamber, warming means located upstream of the said chamber and/or at least one buffer tank, the plant preferably having the compression means, the warming means and the buffer tank placed in series;

control means acting on the compression means in response to a predetermined pressure threshold being detected by at least one pressure sensor designed to be able to determine the pressure obtaining in the said buffer tank.

According to yet another aspect, the invention relates to a plant for filling containers with gas, which comprises:

a manufacturing plant; and conveying and filling means located downstream of the temperature adjustment means and making it possible to convey the gas mixture to at least one gas container to be filled with the said gas mixture and to fill the said container.

Within the context of the present invention, "dynamic mixing" is understood to mean mixing carried out by continuous and/or simultaneous injection of the constituents of the said mixture into a mixing chamber and/or direct injection into packaging containers, and this being achieved with the expected or desired final composition.

The various problems encountered with the conventional packaging processes do not in fact arise with a dynamic mixer according to the invention, this being so for several reasons, and, above all, because the metering of the masses by a mass flowmeter obviates the uncertainties in the temperature and pressure measurements, and the manufacturing vagaries associated with the errors on the measured amounts and values which exist with the said known packaging processes.

The "dynamic" gas mixture packaging process according to the invention is particularly suitable for the production and packaging of gas mixtures intended for use in the medical or pharmaceutical field, which gas mixtures must meet strict requirements in terms of mixture quality and precision, especially for obvious reasons of patient safety.

The dynamic packaging method of the invention is particularly suitable for the manufacture of gas mixtures based on $O_2$, $N_2$, He and $N_2O$, or even $CO_2$ but with a volume content greater than 30%.

The dynamic packaging process, also called dynamic mixing, consists in filling, from the start to the end of the packaging sequence, one or more gas bottles with a gas mixture having the desired final composition.

The gas mixture is produced upstream of the filling injection rail in a very small mixing chamber into which the gases making up the composition of the mixture to be produced are fed, the amounts fed for each gas being monitored by a mass flowmeter assigned to each source of each of the constituents of the gas mixture to be produced.

A set of several control valves is used to control the source gas flow rate by virtue of the action of an automatic control system.

In general, the dynamic packaging process of the invention has the following main advantages:

the packaged mixture is immediately homogeneous, that is to say it does not require the bottles to be subsequently rolled in order to mix and properly homogenize the gases which are in them;

it makes it possible to limit the production variations in the content for a bank of bottles filled during the same filling cycle given that the batch manufactured may be qualified by a single analysis carried out on one bottle of the batch, thus resulting in savings being made both in the cost of analytical testing and in filling time;

mass-based metering of the amounts of gas to be packaged has the advantage of providing measurement accuracy and therefore of metering the amount on each source gas irrespective of the pressure and temperature conditions. The accuracy of mass-based metering therefore makes it possible to achieve an extremely low level of gas mixtures which are scrapped after analytical testing; and the fact of carrying out mass-based metering rather than measuring pressures and temperatures has the advantage of avoiding the measurement errors that can occur in gas mixtures and therefore of solving the problem of obtaining gas mixtures whose contents of the various components of which they are composed do not conform to the desired contents.

In addition, by virtue of the process of the invention, the contents of the various constituents of the said gas mixture within several containers filled during the same filling cycle are reproducible from one container to another, that is to say from gas bottle to gas bottle, since the manufacturing deviations are extremely small from one bottle to another. Consequently, a batch of several bottles filled during the same filling cycle may be checked by analysing a single bottle taken at random from the batch and it is no longer necessary to repeat this check on several bottles, as is usually the case. This makes it possible to save time and to increase the productivity and efficiency of the packaging process.

In other words, a very high level of packaging reproducibility is achieved over time by using a dynamic mixer for packaging gas mixtures, in particular $N_2O/O_2$ gas mixtures.

BRIEF DESCRIPTION OF THE DRAWINGS

The present invention will now be made clearer by the following detailed description of one possible embodiment of a dynamic packaging plant according to the invention and of its operation, as illustrated in the FIGURE appended hereto.

DETAILED DESCRIPTION OF THE INVENTION

A plant according to the invention with a dynamic mixer, allowing $N_2O$ to be put into the supercritical state and subsequently mixed with oxygen in order to produce a 50% $N_2O$+50% $O_2$ binary gas mixture is explained in detail in the FIGURE appended hereto.

This plant comprises, in series, a tank 1 of $N_2O$ stored in liquid form, for example at a temperature of about −20° C. and at a pressure of around 20 bar, which feeds, via its outlet and the line 2, the inlet of a gas compression unit 3 for compressing the liquid $N_2O$ to a maximum pressure of 280 bar, the compression unit being controlled (via 5) by an automatic site control unit 4.

The fluid compressed in 3 is conveyed by the line 6 to a first heater 7, which is electrically operated, allowing the $N_2O$ to be boiled off and heated up, for example to the desired temperature.

A buffer tank 8 having a volume of 500 water-equivalent liters is used to store the heated gaseous $N_2O$ at the desired temperature, for example at about 120° C. on leaving the first heater 7.

A pressure sensor 17 is used to measure the gas pressure in the tank 8, the said sensor 17 being connected via 16 to the automatic control unit 4 so that there is feedback control of the compression means 3 according to the pressure value determined by the sensor 17.

Thus, when the pressure of the gas in the gas tank 8 reaches 280 bar, the compression unit 3 and the heater 7 are turned off and the gas mixture manufacturing unit 10 located downstream of the tank 8 consumes the gas stored in the said tank 8.

Conversely, when the pressure of the gas tank 8 falls below a minimum value, for example 260 bar, the compression unit 3 and the heater 7 are turned on until the tank 8 again reaches 280 bar.

The gaseous $N_2O$ tank 8 feeds the dynamic mixing manufacturing unit 10 via the line 9.

The dynamic mixer 10 then receives $N_2O$ gas at a mean pressure of around 270 bar and at a temperature of about 120° C., on the one hand, and gaseous oxygen at room temperature and at a mean pressure of around 270 bar which comes from a gaseous oxygen source 14 and is conveyed by a line 15, on the other hand.

The gas mixture with the desired $N_2O$ and $O_2$ proportions is then obtained, for example a 50%/50% mixture.

The outlet of the dynamic mixing manufacturing unit 10 is, in accordance with the present invention, connected via a line 11 to a second electric heater 12 intended to keep the gas mixture produced in the unit 10 at a temperature above its demixing point.

Next, the gas mixture is sent via the line 13 to one or more gas containers (not shown) which are filled with the 50%/50% $O_2/N_2O$ gas mixture thus produced.

In this case, the tank 1 containing $N_2O$ in liquid form was chosen because of the advantage of storing liquid $N_2O$ in the case of large consumptions.

However, it goes without saying that bottles or other sources of $N_2O$ in gas form could also be used in the case of lower consumptions and the compression unit 3 could therefore compress gaseous $N_2O$ and the electric heater 7 would merely have the function of warming the said $N_2O$.

Similarly, the oxygen source 14 contains oxygen in gaseous form, but it is conceivable to use liquid oxygen if the consumptions justify it and, in this case, it is possible to provide a third heater in the line 15 so as to boil off and warm the liquid oxygen to the desired temperature, namely the ambient temperature (about 1° C. to 45° C.).

Moreover, electrical energy is chosen for supplying the heaters 7 and 12 because of the energy sources directly available on the application site. However, here again, other energy sources may be used, such as steam, or sources of heat coming from units or processes which generate heat or require cooling.

The filling of containers at pressures below 200 bar could, furthermore, result in the definition of different pressures within the system, especially pressures in the lower lines, for example filling pressures of 150 or 170 bar.

In the light of the foregoing, it will be understood that the first aspect of the invention relates to bringing the gas, $N_2O$ in this case, into the supercritical state for dynamic packaging of the gas mixture.

The second aspect of the invention relates to improving the dynamic packaging of mixtures having a content of more than 30% of liquefied gas, such as the abovementioned 50% $O_2$+50% $N_2O$ analgesic gas mixture.

During filling of the containers, in the absence of the gas warming means 12 located downstream of the mixing chamber 10, because of the expansion of the gases downstream of the said mixing chamber 10, the gas mixtures cool and the temperature reached may be below the demixing temperature of the product to be packaged, thereby degrading the production reproducibility of the mixtures in the various bottles filled from the same injection rail.

Now, in accordance with the invention, by using a heater 12 downstream of the said gas mixing chamber 10, as explained above, this problem is avoided since the temperature is kept permanently above the demixing temperature of the gas product to be packaged.

The invention relies in fact on the judicious use of the behaviour of $N_2O$ in the supercritical state for the purpose of packaging gas mixtures, especially medical gas mixtures or gas mixtures for medical use.

This is because $N_2O$ is a liquefied gas that must also be brought into the supercritical state in order to produce gas mixtures dynamically which are reliable and in accordance with the intended objective, namely to achieve very precise contents which comply with a specification.

The fundamental mechanisms relating to the critical state of $N_2O$ are little known at the present time and do not form part of the present invention since the enthalpy, entropy, pressure and temperature curves for $N_2O$ do not refer to supercritical conditions. Furthermore, nor does the scientific literature refer to the stability of the $N_2O$ molecule and to the non-degradability of $N_2O$ into NO, NOx, $O_2$ under these temperature and pressure conditions, especially about 270 bar and about 120° C.

It should be emphasized that a lower pressure could have been determined in the case of supercritical $N_2O$ as the value of 270 bar was adopted because of the pressure of the $O_2$ source which should allow mixtures to be packaged at about 200 bar.

The dynamic manufacturing unit of the invention makes it possible to manufacture mixtures of various compositions from several single gas sources and at various final container-filling pressures. Preferably, the pressures of the various gas sources are aligned on the maximum pressure necessary, that is to say 270 bar for example.

To verify the non-degradability of $N_2O$ in the supercritical state, tests were carried out and these have shown that the amounts of NO and NOx found in the specimens were below the specified thresholds in the specifications defined by the $N_2O$ Pharmacopoeia and were also below the levels guaranteed by the basic specifications for bulk $N_2O$ at the factory gate, that is to say a NO content of less than or equal to 2 ppm by volume.

By virtue of the invention, the problem of demixing of the gas mixture is solved owing to the use of the device 12 for warming the gases leaving the mixing chamber 10 in order to keep the gas mixture under temperature conditions above the demixing temperature during the container-filling cycle. Since the mixture is thus kept in the gaseous state, the homogeneity of the mixture is maintained and the resulting deviations in contents of the mixture are sufficiently low to allow a batch of bottles to be checked by carrying out an analysis on a single bottle taken from the filling injection rail.

It should be emphasized that, according to the prior art, this problem of demixing after the expansion chamber 10 of the mixer has never appeared when packaging gas mixtures containing less than 30% $CO_2$ since the demixing temperature of a gas containing less than 30% $CO_2$ is about −30° C. This temperature is reached at the outlet of the mixing chamber 10 only for a short period during the packaging phase.

What is claimed is:

1. A process for manufacturing a gas mixture containing at least a first component and at least a second component in predefined proportions, said first and second components selected from the group consisting of $O_2$, $N_2$, He and $N_2O$, the process comprising the steps of:
   (a) dynamically mixing predetermined proportions of at least said first component and said second component to obtain a gas mixture of the desired composition; and
   (b) adjusting the temperature of said gas mixture containing said first and second components obtained in step (a) to keep the temperature above a demixing threshold temperature of said mixture.

2. The process according to claim 1, wherein the second component is chosen from $CO_2$ and $N_2O$ and the content of the second component is greater than or equal to 30 volume %.

3. The process according to claim 1, wherein the first component is oxygen and the second component is nitrous oxide.

4. The process according to claim 1, wherein at least one of said first and second components is in the supercritical state.

5. The process according to claim 1, wherein in step (b), the temperature of the gas mixture is adjusted to or kept above −5.5° C.

6. The process according to claim 1, wherein the temperature of the gas mixture is adjusted by warming the gas mixture by heat exchange.

7. The process according to claim 1, wherein the pressure of the gas mixture is between 120 bar and 300 bar.

8. A process for filling a container with gas comprising injecting a gas mixture containing at least a first component and at least a second component in predefined proportions into at least one container, said gas mixture being obtained by the process according to claim 1.

9. A process for filling a container with gas comprising injecting a gas mixture consisting of 50 vol % oxygen and 50 vol % nitrous oxide into at least one container, said gas mixture being obtained by the process according to claim 1.

10. The process according to claim 1, wherein the content of the second component is at least 40 volume %.

11. The process according to claim 3, wherein the gas mixture consists of 50 volume % oxygen and 50 volume % nitrous oxide.

12. A process for manufacturing a gas mixture containing at least a first component and at least a second component in predefined proportions, said first component selected from the group consisting of $O_2$, $N_2$, He and $N_2O$ and said second component consisting of $CO_2$, the process comprising the steps of:
   (a) dynamically mixing predetermined proportions of at least said first component and said second component to obtain a gas mixture of the desired composition; and
   (b) adjusting the temperature of said gas mixture containing said first and second components obtained in step (a) to keep the temperature above a demixing threshold temperature of said mixture.

13. The process according to claim 12, wherein the gas mixture contains $CO_2$ and $O_2$, and optionally helium.

14. A process for filing a container with a gas comprising injecting a gas mixture containing at least a first component selected from the group consisting of $O_2$, $N_2$, He and $N_2O$ and at least a second component consisting of $CO_2$ in predefined proportions into at least one container, said gas mixture being obtained by the process according to claim 12.

15. The process according to claim 13, wherein the content of $CO_2$ is at least 40 volume %.

* * * * *